United States Patent [19]

Adsara et al.

[11] 4,243,679
[45] Jan. 6, 1981

[54] S-(3-METHYL-2-BUTENYL)CYSTEINE

[76] Inventors: Jorge D. Adsara, 41, calle Dalmases, Barcelona-17, Spain; Silvano Casadio, 11, via Tantardini, Milano, Italy; Jose M. B. Ribalta, 125 bis, calle Mayor de Sarria; Leonida Bruseghini, 53, calle Mayor de Sarria, both of Barcelona-17, Spain

[21] Appl. No.: 31,612

[22] Filed: Apr. 19, 1979

[30] Foreign Application Priority Data

Apr. 22, 1978 [ES] Spain .............................. 469.060

[51] Int. Cl.$^3$ ............................................. A61K 31/195
[52] U.S. Cl. ..................................... 424/319; 562/557
[58] Field of Search ......................... 424/319; 562/557

[56] References Cited

U.S. PATENT DOCUMENTS

| 3,879,560 | 4/1975 | Kalopissis | 562/557 |
| 3,892,852 | 7/1975 | Joullie | 424/319 |
| 3,950,387 | 4/1976 | Joullie | 562/557 |
| 3,950,542 | 4/1976 | Kalopissis | 424/319 |
| 3,984,569 | 10/1976 | Kalopissis | 424/319 |

FOREIGN PATENT DOCUMENTS 2520772  11/1975  Fed. Rep. of Germany ........... 562/557

OTHER PUBLICATIONS

Obata, Agr. Biol. Chem., 29, pp. 104–107 (1965).

Primary Examiner—Natalie Trousof
Assistant Examiner—Michael Shippen
Attorney, Agent, or Firm—Michael J. Striker

[57] ABSTRACT

S-(3-methyl-2-butenyl)cysteine

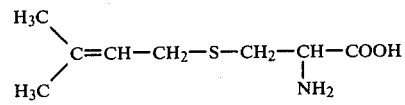

or a pharmaceutically acceptable salt thereof. The compound is an expectorant and can be applied in the form of capsules or dragees, solutions, syrups or suppositories.

1 Claim, No Drawings

S-(3-METHYL-2-BUTENYL)CYSTEINE

BACKGROUND OF THE INVENTION

The present invention relates to a new thioprenyl compound with pharmacological activity, a process for its preparation and pharmaceutical compositions containing it.

The use of drugs acting on the respiratory system mucus is important in therapeutic medicine due to the wide range of afflictions (respiratory air passage infections, respiratory decompensation stages, tumorous growths, allergic reactions, changes in the autonomous nervous system, etc.) in all of which the respiratory tract fluid is altered, this constituting a danger or substantial discomfort to the patient. Within the pharmacological groups related to the tracheo-bronchial mucus are: bronchosecretogogues, expectorants and mucolytics.

The aim of these products is "bronchial-draining". Their main defect, except in case of Bromhexine ("Bisolvon") and S-carboxymethylcysteine, is that they act only by direct aerosolization or instillation in the bronchial system. The toxicity of the vehicles used in aerosol sprays, as in the case of N-acetylcysteine and its derivatives, is subject to the question (see the editorial "Are aerosol sprays hazardous?" *Am. Rev.Resp. Dis.*, 112, 485 (1975)), whether they are not harmful to the bronchial tree; on the other hand, correct administration is not simple and free of risk nor a practice that can be performed outside specialized centers.

The outstanding result in this field is the systemic actuation of Bromhexine ("Bisolvon"), which is well adsorbed when orally administered and has practically no side effects, although its action is not always clear. It has even been argued (J. H. M. Langlans, *Lancet*, 1, 448 (1970) concluding the report of the "Research Committee of the British Thoracic and Tuberculosis Association" (*Br. J. Dis. Chest*, 67, 49 (1973)) that Bromhexine cannot be recommended in routine treatment of bronchitis.

Another compound also acting orally is S-Carboxymethylcysteine, of which, however, doses over one (1) gram per day are needed.

SUMMARY OF THE INVENTION

Investigations were therefore undertaken to obtain a drug with greater activity on the respiratory tract mucus. As a result there was obtained S-(3-methyl-2-butenyl)-cysteine, herein identified as ITA 275, also referred to as 2-amino-3-prenylthiopropanoic acid and S-prenylcysteine, whose chemical and therapeutic properties will be described below.

Its novelty consists basically in the following:

(a) it is active on systemic administration, both orally and parenterally, thus resulting in greater utility and a more convenient application than N-acetylcysteine, which latter is administered only as aerosol.

(b) the experimental results are more definite and more consistent than those obtained with Bromhexine.

(c) its mucolytic potency is superior to that of S-carboxymethylcysteine and it can therefore be administered in smaller doses.

(d) its toxicity is small. It is not toxic orally and when parenterally administered it is of smaller toxicity than S-carboxymethylcysteine.

PROCESS OF MAKING

The compound claimed in the present invention, 2-amino-3-prenylthiopropanoic acid or S-(3-methyl-2-butenyl)-cysteine (ITA 275) is prepared by reaction of a prenyl halide of the formula

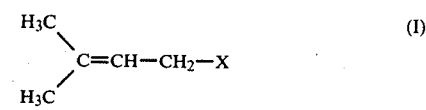

where X is halogen (F, Cl, Br, I) with cysteine of the formula

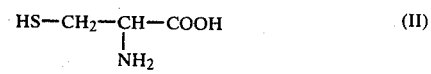

or a compound thereof. By cysteine compound the hydrochloride or an alkalimetal or ammonium salt thereof is understood. Conditions must be such that the species employed in the reaction may be the alkali metal or ammonium cysteine salt. This is accomplished either by using the cysteine salt itself as the starting material or by using cysteine or its hydrochloride in the presence of one or two moles respectively of a neutralizing agent comprised of an alkali metal hydroxide, ammonia, or an alkali metal or ammonium salt of acids having pK values greater than 3.2.

The reaction is carried out by slow addition of the prenyl halide (I) to a stirred solution of the cysteine compound either in water or in hydroalcoholic mixtures, the alcohol being methanol, ethanol, isoropanol, etc., and at the temperature range of 5° to 15° C. When the addition is finished, the mixture is stirred for several hours at the temperature range from 0° C. to boiling. Preferred is operating at room temperature or below since cysteine seems to decompose substantially at temperatures in excess of 20° C.

The white solid which precipitates from the reaction mixture is filtered, washed with water and ethanol and dried, giving a highly pure crystalline residue of the following structural formula:

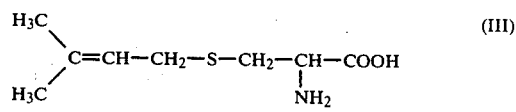

Empirical formula: C$_8$H$_{15}$NO$_2$S Mol. wt.: 189

EXAMPLES

The following examples will further illustrate the invention.

EXAMPLE 1

Preparation of 2-amino-3-prenylthiopropanoic acid and its hydrochloride.

Prenyl chloride (213 g, 2.04 m) was slowly added to a stirred solution of cysteine hydrochloride (300 g, 1.90 m) in 2 N sodium hydroxide (1900 ml) and ethanol (1500 ml) at the temperature of about 5° to 10° C. Before the addition was finished, a white solid started to precipitate. The mixture was stirred overnight at room temperature, and the precipitate was filtered, washed with ethanol and water, and dried. 230 g (64%) of the free acid in the form of a white crystalline solid was obtained, m.p. 190°-4° C. (d) (measured on a Mettler FP5 apparatus, introducing the substance at 170° C. and with a temperature increase of 3° C./min).

Thin layer chromotography (Ethanol/water: 7/3): A single spot develops when sprayed with "ninhydrin" (ninidrine)

Infrared (KBr)

Strong peaks at 1615, 1578, 1480 and 1410 cm$^{-1}$.

Analysis (%) for $C_8H_{15}NO_2S$ (mol. wt. 189.3): Calculated: S 16.96; found: 16.93: Calculated: N 7.40; found: 7.34.

Hydrochloric acid 2 N (4.5 ml) was added to a suspension of the above obtained 2-amino-3-prenylthiopropanoic acid (ITA 275) (1.90 g; 0.01 m) in water (50 ml). Nearly all of the compound was dissolved, the solution was filtered and the mother liquors were used up. 2-amino-3-prenylthiopropanoic acid hydrochloride (1.84 g, 0.08 m; 81% yield) was obtained as a white crystalline solid, m.p. 181°-3° C.

Infrared (KBr)

Strong peaks at 1725, 1490, 1215 and 1190 cm$^{-1}$

RMN (d$_6$-DMSO)

δ 8.78 (wide signal,4,—+$\underline{NH}_3$ and —COO$\underline{H}$); 5.10 (t,1, C=C$\underline{H}$); 3.93 (t,1,—C$\underline{H}$—COOH); 3.17 (d,2, C=CH—C$\underline{H}_2$—S); 2.95

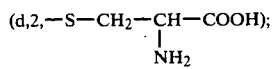

1.62 (d,6, (C$\underline{H}_3$) C=).

EXAMPLE 2

Preparation of 2-amino-3-prenylthiopropanoic acid (ITA 275)

A solution of prenyl chloride (6.31 g; 0.06 m) in ethanol (40 ml) was slowly added to a stirred solution of cysteine hydrochloride (7.9 g, 0.05 m) and Na$_2$CO$_3$. 10 H$_2$O (28.6 g, 0.10 m) in water (130 ml) at 15° C. The mixture was stirred for three hours at room temperature, carefully heated to 80° C., kept at this temperature for half an hour and allowed to stand overnight at room temperature. The white precipitate was filtered, washed with ethanol followed by a water wash and dried. 1.6 g (18%) of a white crystalline solid of the above composition was obtained m.p. 190°-4° C.

PHARMACOLOGICAL ACTIVITY

Tests were carried out with the compound claimed in order to establish its pharmacological and toxicological perimeters. The results are given below.

1. Pharmacodynamics 1.1. Secretogogial Activity

The capacity of increasing tracheobronchial secretion was determined by the technique of bronchial elimination of sodium fluoresceine (Mawatari, Kagoshima Daigak Igaku Zasshi, 27, 561 (1976)) on two animal species and by two different administration routes: oral and parenteral.

In all cases, the compound ITA 275 showed activity, as can be seen from Table I, and since its effect depends on the dose given, the corresponding Effective Dose can be established. Compounds used as standard: Bisolvon (clinically widely used) and S-carboxymethylcysteine (chemically similar to ITA 275); the effects of both compounds were not only less definite than those of ITA 275, but were below statistical significance and did not follow a constant dose-effect sequence.

TABLE I

| | Secretogogue activity - Mawatari's technique Three dose levels  n = 15–40 = number of test animals Male animals were used | | | | | | |
|---|---|---|---|---|---|---|---|
| Treatment | Species | Administration route | Max. efficiency % secretion increase | P | ED$_{25}$ mg/kg | ED$_{50}$ mg/kg | W |
| S. Carboximethylcisteine | Mouse | p.o. | 6,3 | n.s. | no correlation | — | 16,7 |
| Bisolvon | " | p.o. | 34,7 | n.s. | no correlation | — | 20,5 |
| ITA 275 | " | p.o. | 20,7 | <0,1 | 611 | — | 21,3 |
| S. Carboxi. . | " | i.p. | 22,3 | n.s. | 764 | — | 17,3 |
| Bisolvon | " | i.p. | 26,0 | n.s. | 32 | — | 13,5 |
| ITA 275 | " | i.p. | 42,7 | <0,001 | 218 | — | 13,7 |
| S. Carboxi. . | Rat | p.o. | 39,3 | <0,1 | — | 1071 | 144,8 |
| Bisolvon | " | p.o. | 14,8 | n.s. | — | no correlation | 62,2 |
| ITA 275 | " | p.o. | 57,0 | <0,1 | — | 447 | 127,1 | p = statistical probability that the results are due to chance
W = average weight of the animals (g)

1.2. Expectorant activity

Determination of the expectorant activity was achieved by the technique of collecting mucus of anaesthetized rabbits breathing in conditioned air at body humidity and temperature (Perry and Boyd, J. Pharmacol. Exp. Ther., 23 65(1941)), and measuring the percentage increase of fluid collected in relation to controls.

The results of comparing ITA 275 with the two standards used before, appear in Table II which show that the claimed compound is somewhat more active than S-carboxymethylcysteine, having a greater statistical significance, (shown by p, that has the same meaning as in Table I).

Table II

| | Expectorant activity. Perry-Boyd technique, in rabbit. Oral route,  n = 12 = number of test animals | | | | |
|---|---|---|---|---|---|
| Treatment | Dose mg/kg p.o. | % increase with regard to controls | sex | P | W |
| Bisolvon | 20 | 20,6 | both | n.s. | 1,85 |
| Bisolvon | 40 | 38,1 | " | n.s. | 1,74 |

Table II-continued

| Expectorant activity. Perry-Boyd technique, in rabbit. Oral route, n = 12 = number of test animals | | | | | |
|---|---|---|---|---|---|
| Treatment | Dose mg/kg p.o. | % increase with regard to controls | sex | P | W |
| S. Carboxymethylcysteine | 500 | 110,9 | " | <0,005 | 1,85 |
| ITA 275 | 500 | 135,6 | " | <0,001 | 1,80 |

W = Average weight of the animal (Kg)

1.3. Modification of the respiratory mucus composition

By means of an original technique (Giraldez and Gras), XXVI Congr. IUPS, Abstr. 777, Paris 1977)) which allows the collection of abundant samples of mucus on conscious animals and on consecutive days, the amount of eliminated mucus, its biochemical composition and its physico-chemical constants were studied. In addition to the two standards used before, N-acetylcysteine was also administered by topic route.

The results, which appear in Table III, show that ITA 275 caused a great increase in mucus elimination as well as an increase in the content of total proteins, and on the other hand, does not present the mucolytic property of N-acetylcysteine demonstrated by the release of -SH groups.

TABLE III

| Modification of mucus composition. Giraldez-Gras Method, in rabbit Oral route n = 12–30 = number of test animals | | | | | | | |
|---|---|---|---|---|---|---|---|
| Treatment | Dose mg/kg | % Increase mucus weight | total proteins | Mucoproteins | -SH Groups | sex | W |
| Blank | — | −21,3 ± 0,1 | 10,4 ± 40,0 | 37,8 ± 22,6 | −12,5 ± 7,2 | both | 2,02 |
| Vehicle | 2 ml/kg | 77,3 ± 39,8 | 69,9 ± 75,3 | −0,2 ± 33,3 | 13,7 ± 19,3 | " | 2,60 |
| N-acetylcysteine | 0,1ml/kg sol. 20% (topic) | 150,9 ± 30,8 | 491,4 ± 311,1 | 2450,3 ± 480,5** | 305,5 ± 102,9* | " | 2,18 |
| S-Carboxymethylcysteine | 500 | 16,4 ± 44,9 | 31,7 ± 27,4 | 131,9 ± 91,8*** | 11,6 ± 34,2 | " | 1,84 |
| Bisolvon | 40 | −6,1 ± 8,3 | 3,1 ± 14,4 | 4,9 ± 8,9 | 0,3 ± 13,4 | " | 1,87 |
| ITA 275 | 500 | 466,1 ± 343,5 | 113.8 ± 93,7 | 32,7 ± 14,3 | 29,2 ± 14,4 | " | 2,02 |

*p < 0,1
**p < 0,01
***p < 0,005
W = Average weight of the animals (Kg)

1.4. Effect on the ciliary movement

The effect of the drug solution on the transport time by ciliary epithelium was determined in the isolated dog trachea measuring the displacement of charcoal particles impelled by ciliary movement in a given time and comparing them with d-tubocarine; the vehicle used for dissolving the compounds was a buffer solution (pH=7.4), prepared by diluting to 100 ml., 19.6 mg of a 1/13 M solution of $KH_2PO_4$ with 1/15 M $Na_2HPO_4$. This vehicle was also used as the blank.

The increase in transport time due to ITA 275, which lasted at least 20 min., is shown in Table IV. Animals of both sexes were used.

TABLE IV

| Mucus transport time, in isolated dog trachea n = 5 = number of test animals | | | | | |
|---|---|---|---|---|---|
| Treatment | conc. | % increase of ciliary transport time min. | | | |
| | | 0 | 10 | 20 | W |
| Buffer | — | 44,1 ± 14,5 | 26,4 ± 15,6 | 13,0 ± 10,4 | 13 |
| d-turbocurarine | $10^{-4}$ g/ml | 69,8 ± 12,3 | 32,3 ± 14,5 | 28.7 ± 19,7 | 11 |

TABLE IV-continued

| Mucus transport time, in isolated dog trachea n = 5 = number of test animals | | | | | |
|---|---|---|---|---|---|
| Treatment | conc. | % increase of ciliary transport time min. | | | |
| | | 0 | 10 | 20 | W |
| ITA 275 | 10 mM | 162,3 ± 13,4 p<0,001 | 107,3 ± 21,8 p<0,01 | 16,2 ± 7,6 | 11 |

W = Average weight of the animals (Kg)

2. Toxicology

2.1. Acute toxicity

The results are shown in Table V.

The compound ITA 275 has a very low acute toxicity both by oral and intraperitoneal routes on the two species studied, it being even smaller than that of S-carboxymethylcysteine.

The weight of the animals was of 180±20 g for rats and >25 g for mice.

TABLE V

| Compound | Animal | Route | $LD_{50}$ (mg/kg) and confidence limits | n ♂ | ♀ |
|---|---|---|---|---|---|
| ITA 275 | Rat | p.o. | >4000 | 10 | 10 |
| | | i.p. | 3095 (2399–3993) | 30 | 40 |
| | Mouse | p.o. | >4000 | 10 | 10 |
| | | i.p. | 2090 (1780–2454) | 50 | 40 |
| S-Carboxymethylcysteine | Rat | p.o. | >4000 | 10 | 10 |
| | | i.p. | 2480 (2193–2805) | 40 | 40 |
| | Mouse | p.o. | >4000 | 10 | 10 |
| | | i.p. | 1785 (1475–2160) | 60 | 50 | n = number of test animals

2.2. Subacute toxicity in rat

In order to study the toxicity of ITA 275 in the rat, this compound was given at doses of 100, 300 and 1000 mg/kg/day during one month, to 100 rats (♂/♀ =50/50)

The treatment did not modify either the weight increase or the food and water intake. The hematological values remained normal.

A slight increase in liver weight was found; all other organs did not undergo weight changes.

No abnormalities in the general behaviour of rats given ITA 275 was observed.

ITA 275 was well tolerated by rats receiving doses of up to 1000 mg/kg/day during one month.

2.3. Subchronic toxicity in rat

ITA 275 was given during six months to rats at the same doses as in the preceding test. The number of animals used was of 100 (♂/♀ =50/50).

The compound was well tolerated by the rats treated over a period of six months.

THERAPEUTICAL USES

The use of the claimed mucolytic compound is recommended in all types of rhinitis, sinusitis, tracheitis, pharyngitis, bronchitis, tracheobronchitis, bronchiectasies, bronchopneumonia, chronic bronchopneumopathies, smokers' bronchial catarrh, etc., as well as in preparation of respiratory-tract surgical operations such as tracheotomy and prevention of postoperative respiratory complications, prevention of influenza bronchial complications, infectious illnesses, etc.

It can also be used in preparation for respiratory-tract surgical operations, in tracheotomy, to prevent influenza-bronchial complications, infection caused illness, etc.

ADMINISTRATION

There are different administration forms: inhalations, nebulizations, aerosols, direct instillations of suspensions and solutions, syrups, capsules, dragees, suppositories, etc.

In the case of solutions, these will be prepared from salts, such as the hydrochloride or its alkaline salts.

THERAPEUTICAL DOSAGE

The following dosage for the different administration forms is recommended:

Capsules and dragees (100 to 500 mg): 2 to 6 dragees per day depending on age.

Solutions (2 to 5%)—(oral administration):

1 spoonful (5 or 15 cc depending on age), three times per day.

Solutions (10 to 20%)—(nebulizations or direct instillations).

Syrups (2 to 5%)—1 spoonful (5 to 15 cc depending on age), three times per day.

Suppositories—(100 to 500 mg) two per day.

In all cases, the appropriate excipients should be added.

EXAMPLE 3

| Dragrees - composition for one dragee | mg. |
| --- | --- |
| ITA 275 | 100 |
| active charcoal | 2 |
| Mg stearate | 2 |
| starch | 200 |
| lactose | 200 |
| -cover of one dragee | |
| gelatine:sugar:talc:starch:arabic gum - 5:30:30:30:5 | |
| sufficient amount to make to a total weight of 750 mg. | |
| Capsules - composition for one capsule (n.O) | mg. |
| ITA 275 | 100 |
| active charcoal | 3 |
| methyl salicylate | 0.15 |
| mint perfume | 2 |
| lactose:sufficient amount to make a total weight of 300 mg. | |
| Suppositories - composition for one suppository | mg. |
| ITA 275 | 100 |
| active charcoal | 7.5 |
| saturated triglycerides mixture: sufficient amount to make a total weight of 2.5 g. | |

In actual use details not affecting the essentials of the invention may of course be changed within the scope of the appended claims.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. A method of treating a patient for fluidification and removal of tracheabronchial mucus, pathological substances and foreign bodies from the respiratory tract comprising administering orally, by inhalation or per rectum daily dosages of 200 mg to 3.00 g S-(3-methyl-2-butenyl)-cysteine.

* * * * *